United States Patent [19]

Hakki

[11] Patent Number: 4,901,721
[45] Date of Patent: Feb. 20, 1990

[54] SUTURING DEVICE

[76] Inventor: Samir I. Hakki, 8547 Merrimoor Blvd. E., Largo, Fla. 33543

[21] Appl. No.: 227,230
[22] Filed: Aug. 2, 1988
[51] Int. Cl.$^4$ .................. A61B 17/08; B65D 63/10
[52] U.S. Cl. .................................. 606/103; 24/27; 606/232; 606/224
[58] Field of Search ............... 128/335, 339; 24/205, 24/27, 30.5 P

[56] References Cited

U.S. PATENT DOCUMENTS

| 1,237,034 | 8/1917 | Harris | 24/27 |
| 1,277,077 | 8/1918 | Ireland | 24/27 |
| 1,474,372 | 11/1923 | Larcott | 24/27 |
| 2,582,093 | 1/1952 | Ayers | 24/27 |
| 4,423,538 | 1/1984 | Saylor | 24/27 |
| 4,730,615 | 3/1988 | Sutherland et la. | 128/335 |

FOREIGN PATENT DOCUMENTS 2553154 4/1985 France .................. 24/20 S
2188237 9/1987 United Kingdom ........ 128/335

OTHER PUBLICATIONS

B. M. Wroblewski et al., "Reattachment of the Greater Trochanter After Hip Replacement", *The Journal of Bone and Joint Surgery*, Nov. 1985, pp. 736–740.

Primary Examiner—Edward M. Coven
Assistant Examiner—Gary Jackson
Attorney, Agent, or Firm—Seidel, Gonda, Lavorgna & Monaco

[57] ABSTRACT

A surgical suturing device for cardio-thoracic surgery and the like has a wire suture and a biasing mechanism operatively connected to one end of the suture. The biasing mechanism has suture receiving structure operatively associated with it and adapted and arranged (1) to cause the suturing device to cinch tightly when the suture is received in the suture receiving structure and (2) to allow limited movement of the bodily tissue sutured thereby.

14 Claims, 3 Drawing Sheets

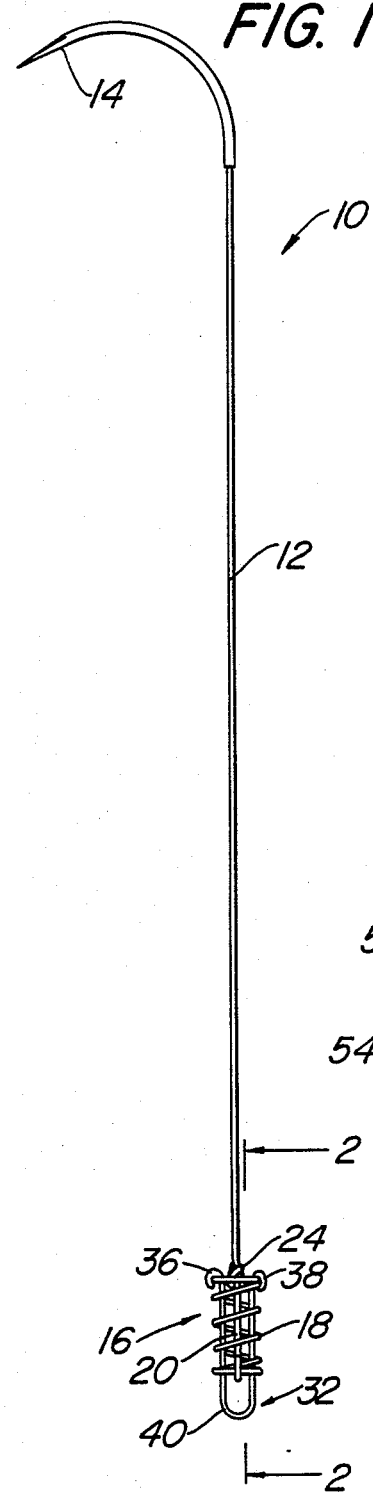
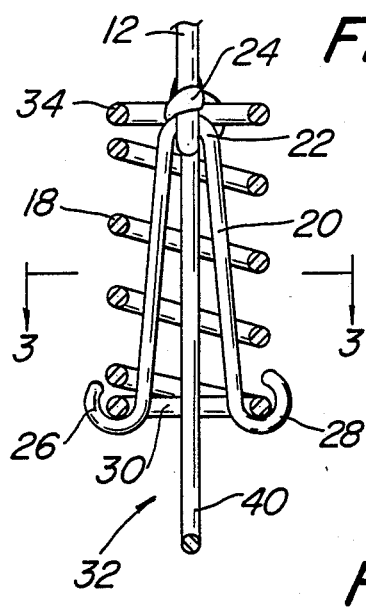
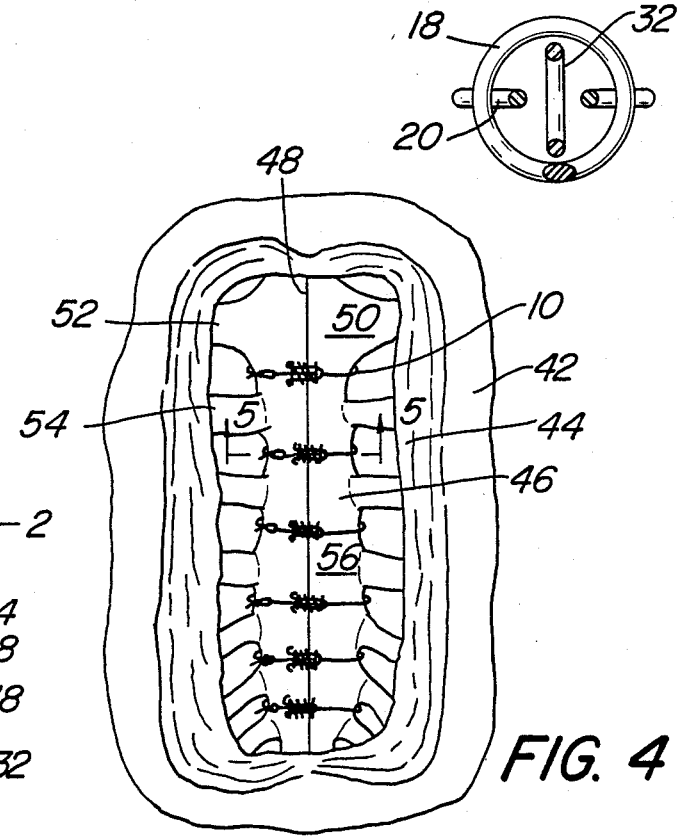

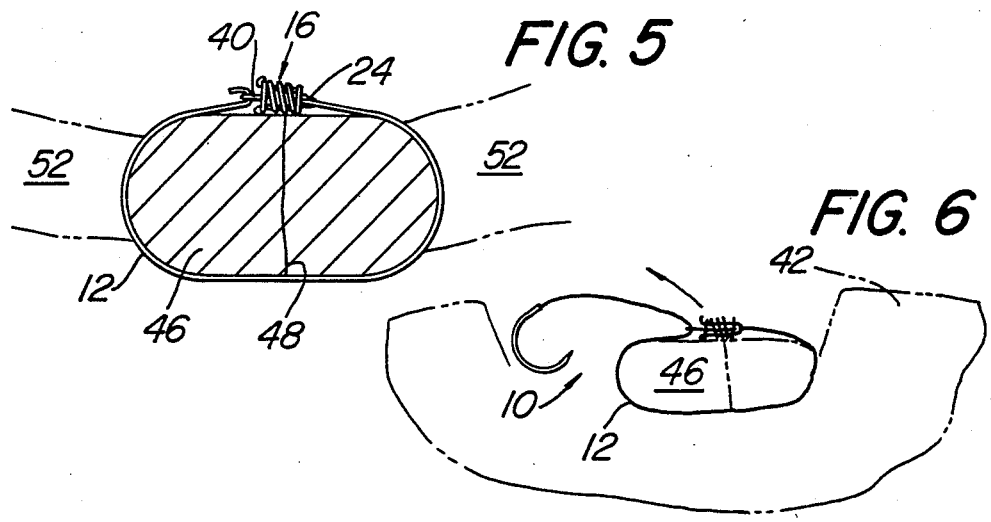
FIG. 5
FIG. 6
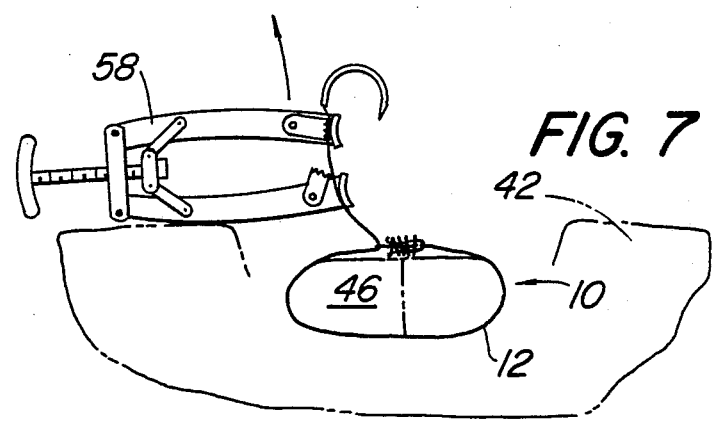
FIG. 7
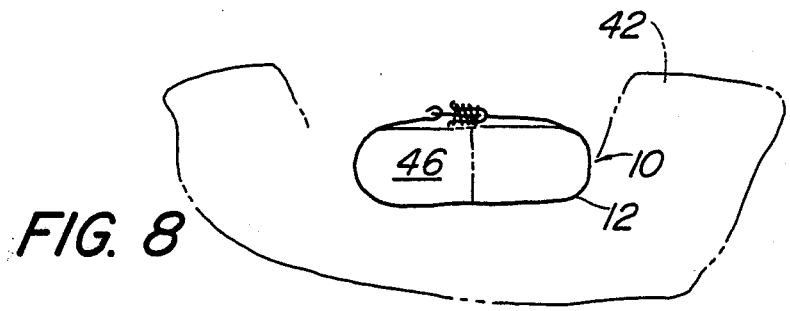
FIG. 8

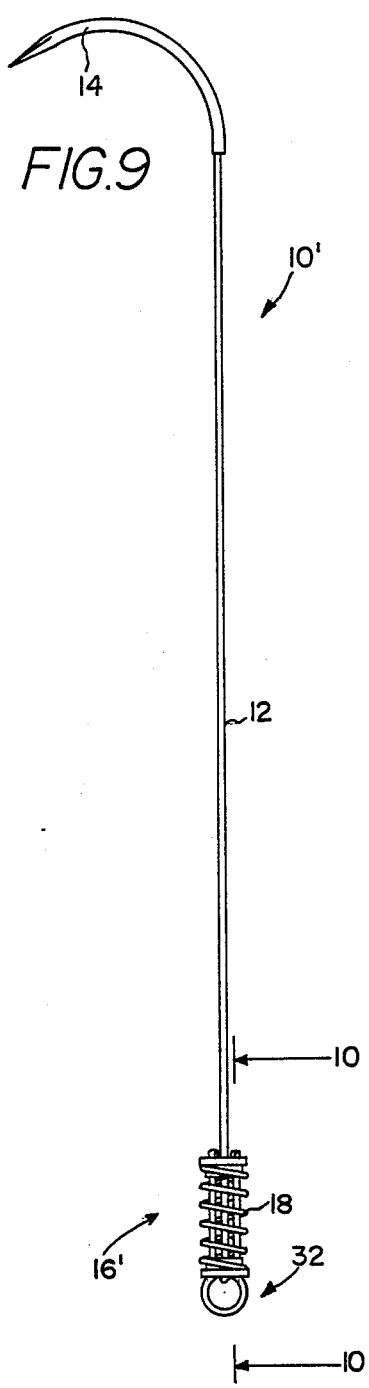
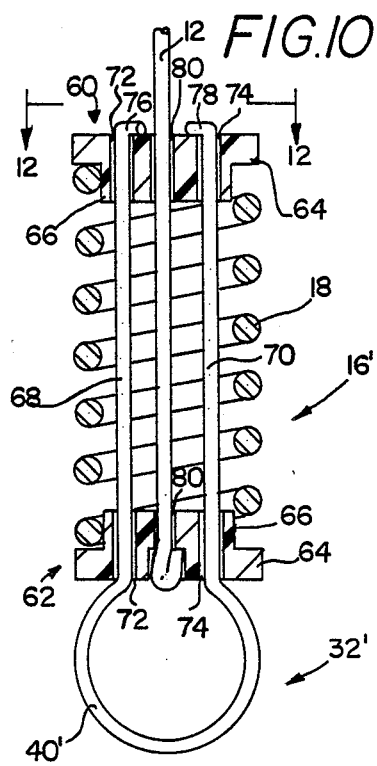
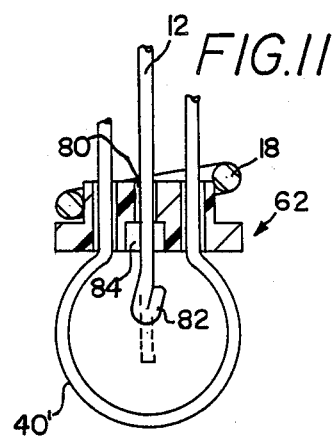
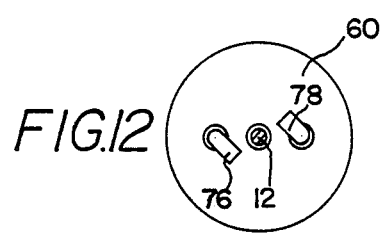

SUTURING DEVICE

FIELD OF THE INVENTION

The invention relates to a suturing device for use in surgery, and is especially useful in cardio-thoracic and orthopedic surgery and the like.

BACKGROUND OF THE INVENTION

Sutures for cardio-thoracic surgery are known. Typically, such sutures consist of a length of wire terminating in a curved needle. The curved needle is used to pass the suture through and/or around tissue (including bone) to be sutured. The needle is inserted into the tissue on one side of the incision to be closed and brought out on the other side of the incision. The free end of the wire remains outside the incision. After passing it through the tissue, the needle end is removed with wire snips and the two ends of the wire are drawn together to cinch the suture and then twisted tightly to hold the suture in place.

A drawback of this unknown type of suture is that, in many cases, as the incision heals the tissue immediately surrounded by the wire suture recedes from the suture. This frequently occurs in thoracic surgery, wherein the wire suture is passed through or around the sternum. In many cases bone necrosis will occur and the sternum will recede from the suture, with the result that a suture which was tightly cinched at the start will become loose as the sternum recedes from the suture. This reduces the effectiveness of the suture and can cause pain or discomfort to the patient or even instability of the sternum.

Another disadvantage of the known type of suture is that, once it is tightly cinched, it will not yield. To achieve stability with known sutures, it is necessary to tighten the wires of to the maximum tension possible. If the patient coughs persistently, this results in higher tension on the wires and pressure on the sternum as it moves during coughing. This will increase the change of breakage of the sutures at the junction where the wires are twisted. Moreover, the sutures are subject to loosening if the patient is osteoporotic, the sternum could collapse from the pressure.

The number of known sutures required to achieve stability is also higher than need be. Six to eight known sutures are required in most cases. The present invention is intended to reduce that number substantially.

A further drawback of known sutures is that it is impossible to get a quantitative measurement of the tension put on the wires. Thus, it is possible to put the sutures under too much or too little tension for a particular patient.

Known sutures also tend to be unstable when passed around, rather than through, the sternum.

There is a need for a suturing device which will overcome these and other disadvantages.

SUMMARY OF THE INVENTION

The present invention is a surgical suturing device which comprises a wire suture, a longitudinally-oriented biasing means for cinching the wire suture tightly around the bodily tissue immediately surrounded by the surgical device, and a suture receiving means, for passing one end of the wire suture therethrough. The biasing means is operatively connected to one end of the wire suture. The suture receiving means is operatively connected to the end of the biasing means opposite that at which the wire suture is connected.

In the disclosed embodiments of the invention, the suturing device comprises a wire suture connected at one of its end to one end of a spring means and having suture receiving means connected to the opposite end of the spring means. The spring means is adapted and arranged to cause the suturing device to cinch tightly when the suture is received in the suture receiving means.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 1 illustrates a suturing device in accordance with one embodiment of the present invention.

FIG. 2 is a sectional view of a portion of the suturing device of FIG. 1, taken along the lines 2—2 of FIG. 1, and showing the biasing means in greater detail.

FIG. 3 is a sectional view of a portion of the suturing device of FIG. 1, taken along the lines 3—3 in FIG. 2.

FIG. 4 is a simplified illustration of the suturing device according to the present invention as used in thoracic surgery.

FIG. 5 is a partial sectional view taken along the lines 5—5 of FIG. 4.

FIGS. 6-8 illustrate a way in which the suturing device of the present invention may be used in cardio-thoracic surgery.

FIG. 9 illustrates a suturing device in accordance with a second embodiment of the present invention.

FIG. 10 is a sectional view of a portion of the suturing device of FIG. 9, taken along the lines 10—10 of FIG. 9, and showing the biasing means in greater detail.

FIG. 11 is a partial sectional view of the biasing means as shown in FIG. 10, illustrating the attachment of the suture to the biasing means.

FIG. 12 is a top plan view of the biasing means, taken along the lines 12—12 in FIG. 10.

DETAILED DESCRIPTION OF THE INVENTION

Referring now to the drawings, wherein like numerals indicate like elements, there is shown in FIG. 1 a suturing device 10 in accordance with one embodiment of the present invention. Suturing device 10 comprises a wire suture 12 which has a needle 14 at one end. Needle 14 is preferably curved to facilitate threading of wire suture 12 through tissue to be sutured, as will be understood by those skilled in the art. Those skilled in the art will also understood that needle 14 may be omitted without departing from the invention.

Wire suture 12 is preferably made of stainless steel or other suitable surgical material compatible with human tissue and is preferably between 150 and 200 mm in length, although the precise length is not critical to the present invention. The diameter of wire suture 12 is preferably on the order of 1 mm, enough to impart some stiffness to wire suture 12, but the diameter of wire suture 12 is otherwise not critical to the invention. The diameter of needle 14, when needle 14 is provided, is preferably the order of 2 mm so that needle 14 possesses the requisite strength and rigidity to enable it to easily pierce and pass through the tissue (including bone) being sutured.

At the end of wire suture 12 opposite needle 14 is a biasing means 16. In this embodiment, biasing means 16 comprises a coil spring 18. Spring 18 is preferably constructed of stainless steel or other suitable wire having a diameter on the order of 2 mm. The outer diameter of spring 18 is preferably on the order of 5 mm to 7 mm. The inner diameter of spring 18 is preferably on the order of 3 mm to 5 mm. The preferred dimensions of spring 18 are believed to provide the strength and resiliency required for suturing device 10, and to provide mobility and ease of compression during application. The preferred spring has at least 30 lbs. of compressive force, i.e., 30 lbs. of force are needed to fully compress it. The precise dimensions and stiffness of spring 18 are not, however, critical to the present invention.

As seen in FIG. 2, wire suture 12 is operatively connected to biasing means 16 by means of V-shaped member 20. Wire suture 12 is attached to the apex 22 of V-shaped member 20. Wire suture 12 may be attached to V-shaped member by any suitable means such as, for example, twisting the end of wire suture 12 around the apex to form a knot 24. Preferably, wire suture 12 is attached to apex 22 of V-shaped member 20 such that relative movement between wire suture 12 and V-shaped member 20 is possible, but is attached so that wire suture 12 cannot pull free of V-shaped member 20.

The ends 26 and 28 of V-shaped member 20 opposite apex 22 are attached to one end of coil spring 18. As best seen in FIG. 2, ends 26 and 28 can simply be bent around end 30 and crimped to permit relative movement between V-shaped member 20 and spring 18.

A suture receiving means 32 is also attached to biasing means 16. As best seen in FIGS. 1 and 2, suture receiving means 32 is in the form of an elongated U-shaped member which is attached to spring 18 at the end 34 thereof opposite the end 30. The open ends 36 and 38 of the U-shaped member may be bent over and crimped to end 34 in a manner analogous to the way in which ends 26 and 28 of V-shaped member 20 are attached to end 30 of spring 18. This enables relative movement between suture receiving means 32 and spring 18. The closed end, or bight, of the U forms a loop 40 for receiving wire suture 12, as will be described in greater detail below. Preferably, both V-shaped member 20 and suture receiving means 32 are coaxial with spring 19 and contained within the inner diameter of spring 18, as best seen in FIG. 3. V-shaped member 20 is preferably of a length such that its entire length is less than the length of spring 18, while suture receiving means 32 is of a length greater than the length of spring 18 so that a sufficient length of suture receiving means 32 extends past the end 30 of spring 18 to form loop 40.

FIGS. 4 and 5 show the suturing device of the present invention as it would be used in cardio-thoracic surgery. FIG. 4 shows an anterior portion of a patient's chest 42 with the skin and sternal portions of the pectoralis major 44 dissected away to expose the sternum 46. As those skilled in the art will appreciate, in cardio-thoracic surgery it is necessary to split the sternum along a medial line 48 to provide access to the interior of the chest, or thorax. After surgery, the halves of the sternum must be sutured. FIG. 4 shows a plurality of suturing devices according to the invention emplaced about the sternum. One suturing device may be placed around the manubrium 50 between the the first rib 52 and second rib 54. Additional suturing devices may be placed around the gladiolus 56 between successive pairs of ribs. The number of suturing devices needed will be less than the number of known sutures needed, but the exact numbers are not critical to the invention.

FIG. 5 is a transverse section through gladiolus 56 between the second and third ribs, showing the suturing device tightly cinched around gladiolus 56 after surgery. Although the skin and the pectoralis major are not shown in FIGS. 4 or 5, thus making it appear as though biasing means 16 is located immediately adjacent the anterior portion of the sternum, it will be recognized by those skilled in the art that the biasing means 16 of the suturing devices will be external to the sternum and pectoralis major but underneath the skin and fat.

FIGS. 6-8 illustrate the way in which the suturing device of the present invention can be sued in cardio-thoracic surgery. The suturing device is threaded through the patient's chest and passed either through or around the sternum 46 so that wire suture 12 is in intimate contact with the lateral and posterior portions of the sternum and so that biasing means 16 remains outside and adjacent the anterior surface of the sternum and the pectoralis major. As wire suture 12 is brought out of the anterior surface of the pectoralis major, it, along with needle 14, is passed through loop 40 of suture receiving means 32. Suture 12 is then pulled to cinch it tightly. Suture 12 may be pulled manually or, preferably, by means of a known spreading tool 58, as shown in FIG. 7. Suture 12 is pulled tightly so that spring 18 is at least partly compressed. While spring 18 is compressed, suture 12 is bent at an acute angle around loop 40. Because of the inherent stiffness of wire suture 12, the suturing device will be held in place by bent portion of wire suture 12 and loop 40. The needle end 14 may then be removed by wire snips, leaving less than an inch beyond loop 40.

The extra stability which the present suturing device provides allows the suturing device to be passed around the sternum, rather than requiring the suture to be passed through the sternum. This gives the surgeon a choice in locating the sutures. In addition, a spring scale or other force measuring device can be readily employed with the present suturing device to give the surgeon a quantitative indication of the tension placed on the biasing means, and hence the suturing device. This gives the surgeon the ability to choose a low tension for patients who have a small sternum or who are osteoporotic and a higher tension in other cases.

It will be appreciated that, since spring 18 is in compression after the suturing device is in place, should the sternum receded from suture 12 during healing, spring 18 is able to expand in order to keep suture 12 tightly cinched. That is, as ends 30 and 34 of spring 18 move apart as spring 18 expands, loop 40 will move toward knot 24, keeping the suturing device tightly cinched. In addition, if spring 18 is only partially compressed when the suture is emplaced, when the patient coughs, the spring 18 can absorb at least some of the movement of the sternum, so that the suturing device can yield slightly to minimize pain to the patient, irritation to and tension on the sternum and tension on the wire connection. The suturing device will also automatically return to a tightly cinched condition as spring 18 expands again.

An alternate embodiment of suturing device of the present invention is illustrated in FIGS. 9 through 12, and is designated by reference numeral 10'. In FIGS. 9 through 12, where elements of suturing device 10' are identical to elements of suturing device 10 illustrated in FIGS. 1 through 3, they are designated by identical reference numerals.

Referring now to FIG. 9, suturing device 10' comprises a wire suture 12 with a need 14 at one end. At the end of wire suture 12 opposite needle 14 is biasing means 16'. As with the first embodiment, in this embodiment biasing means 16' comprises a coil spring 18. As best seen in FIG. 10, biasing means 16' also comprises a pair of end caps 60 and 62 at opposite ends of coil spring 18. Each of end caps 60 and 62 has a flange portion 64 and a reduced-diameter body portion 66. Preferably, the outer diameter of flange portion 64 is approximately equal to the outer diameter of spring 18, while the outer diameter of body portion 66 is approximately equal to the inner diameter of spring 18. Ideally, the outer diameter of portion 66 is slightly greater than the inner diameter of spring 16, enabling the end caps to be press-fit into the ends of spring 18 and enabling the end caps to be held in placed by a snug friction fit. Also, the outer diameter of flanges 64 is ideally slightly less than the outer diameter of spring 18 so that flanges 64 will not project beyond the outer diameter of spring 18. End caps 60, 62 may be made of any suitable surgical material compatible with human tissue, and may, for example, be conveniently molded from an inert polymeric material such as Teflon.

Biasing means 16' is, like biasing means 16, provided with a suture receiving means, designated in this embodiment by reference numeral 32'. As seen in FIG. 10, suture receiving means 32' comprises a wire loop 40, having extended legs 68, 70 which extend upwardly (as shown in FIG. 10) through end cap 62, the interior of spring 18 and end cap 60. End caps 60 and 62 are provided with through bores 72 and 74 through which legs 68 and 70 pass, respectively. Ends 76 and 78 of legs 68 and 70, respectively, may be bent over or crimped, as shown in FIG. 10, to secure suture receiving means 32' to end cap 60 and, thus, to biasing means 16'.

Although biasing means 16' is shown in the figures after attachment to suture 12, it will be appreciated that biasing means 16' may, and preferably is, constructed as a separate unit. This enables biasing means 16' to be supplied separate from suture 12, thus permitting biasing means 16' to be used with any type of suture 12. Biasing means 16' can thus be attached to whatever suture 12 may be chosen by a surgeon at the time the suture is emplaced by the surgeon.

The way in which biasing means 16' can be attached to suture 12 is best illustrated in FIGS. 10 and 11. As seen in those figures, end caps 60 and 62 are each provided with a central bore 80 through which the shank of suture 12 can be passed. The diameter of bore 80 is preferably only slightly larger than the diameter of the shank of suture 12. As shown in FIG. 10, the shank of suture 12 is passed downwardly through end cap 60, the interior of spring 18 and end cap 62. The shank of suture 12 is passed through end cap 62 a short distance into the bight of loop 40', as best seen shown in phantom in FIG. 11. End 82 of suture 12 is then bent over or crimped, effectively at least doubling its diameter and preventing suture 12 from being withdrawn. End cap 62 is provided with a counter bore 84 on bore 80 to receive crimped end 82.

Suturing device 10' can now be used in the same manner as described for suturing device 10. When suture 12 is passed through loop 40' of suture receiving means 32' and pulled tightly, spring 18 will be at least partly compressed because of the oppositely-directed forces acting on spring 18. As suture 12 is pulled tightly, crimped end 82 exerts a force upwardly (as viewed in FIG. 10) on spring 18 while the portion of the suture received in loop 40' exerts a force downwardly on loop 40'. The downward force on loop 40' urges end cap 60 downwardly at the same time the upward force urges end cap 62 upwardly, tending to compress spring 18.

Except for the differences in biasing means 16', suture 10' is identical to, and is used in the identical manner as, suture 10.

The suturing device of the present invention is not limited to cardio-thoracic surgery, but is also suitable for orthopedic surgery, such as osteotomy reattachment for the greater trochanter.

The present invention may be embodied in other specific forms without departing from the spirit or essential attributes thereof and, accordingly, reference should be made to the appended claims, rather than to the foregoing specifications, as indicating the scope of the invention.

I claim:

1. A surgical device for suturing together bodily tissue, which allows limited movement of the bodily tissue sutured thereby, said surgical device comprising:
   (a) a wire suture having a first end and a second end, wherein said first end comprises a needle;
   (b) a longitudinally-oriented biasing means for cinching said wire suture tightly around the bodily tissue immediately surrounded by said surgical device, said biasing means having a first end and a second end, wherein said biasing means first end is operatively connected to said wire suture second end; and
   (c) a suture receiving means for passing said wire suture first end therethrough, said suture receiving means being operatively connected to said biasing means second end, and said suture receiving means and said biasing means being arranged such that pressure is exerted on said biasing means when said wire suture is cinched tightly around the tissue immediately adjacent to said surgical device.

2. A surgical device according to claim 1, wherein the biasing means comprises spring means.

3. A surgical device according to claim 2, wherein the spring means comprises a coil spring.

4. A surgical device according to claim 3, wherein the coil spring is adapted to be in compression when the suture is received in the suture receiving means.

5. A surgical device according to claim 1, wherein the suture receiving means comprises loop means.

6. A surgical device according to claim 1, wherein the wire suture second end is operatively connected to the end of the biasing means farthest from the wire suture first end and wherein the suture receiving means is operatively connected to the end of the biasing means opposite to the end at which the wire suture second end is connected.

7. A surgical device according to claim 6 wherein the wire suture second end is operatively connected to the biasing means by a V-shaped member, wherein the wire suture second end is fixed to the apex of the V-shaped member and wherein the ends of the V-shaped member, opposite the apex, are fixed to the end of the biasing means farthest from the wire suture first end.

8. A surgical device according to claim 7 wherein the suture receiving means is in the form of an elongated U-shaped member which is operatively attached to the end of the biasing means opposite of that at which the ends of the V-shaped member are attached.

9. A surgical device according to claim 8 wherein the biasing means comprises a coil spring and wherein the V-shaped member and the elongated U-shaped member are contained within the inner diameter of the coil spring.

10. A surgical device according to claim 6 wherein the biasing means is a coil spring comprising a first and second end cap operatively connected to opposite ends of the coil spring, each of the end caps having a flange portion and a reduced-diameter body portion wherein the outer diameter of the flange portion is greater than the inner diameter of the coil spring and is approximately equal to the outer diameter of the coil spring, and wherein the outer diameter of the body portion is dimensioned to fit within the inner diameter of the coil spring.

11. A surgical device according to claim 10 wherein the wire suture second end passes through the first end cap, located on the end of the coil spring closest to the wire suture first end, and is operatively connected to the second end cap.

12. A surgical device according to claim 11 wherein the ends of the suture receiving means pass through the second end cap, located on the end of the coil spring farthest from the wire suture first end, and are operatively connected to the first end cap.

13. A method for suturing together bodily tissue with a surgical device which allows limited movement of the bodily tissue sutured thereby, wherein said surgical device comprises: a wire suture having a first end and a second end, wherein said first end comprises a needle; a longitudinally-oriented biasing means for cinching said wire suture tightly around the bodily tissue immediately surrounded by said surgical device, said biasing means having a first end and a second end, wherein said biasing means first end is operatively connected to said wire suture second end; and a suture receiving means, for passing said wire suture first end therethrough, being operatively connected to said biasing means second end, said suture receiving means and said biasing means being arranged such that pressure is exerted on said biasing means when said wire suture is cinched tightly around the tissue immediately adjacent to said surgical device, said method comprising:

(a) passing said wire suture first end through or around the bodily tissue to be sutured such that the wire suture is in intimate contact with the lateral and posterior portions of the tissue to be sutured;

(b) passing said wire suture first end through said suture receiving means;

(c) cinching said wire suture such that tension is placed on said biasing means; and (d) attaching a portion of the wire suture which is passed through said suture receiving means to a portion of the wire suture which is not passed through said suture receiving means.

14. A method as in claim 13 wherein after said wire suture first end is passed through said wire receiving means a force measuring device, which provides a quantitative indication of the tension placed on said biasing means, is used to cinch said wire suture tightly around said bodily tissue and simultaneously exert a tension on said biasing means.

* * * * *